(12) United States Patent
Wanner et al.

(10) Patent No.: US 11,435,302 B2
(45) Date of Patent: Sep. 6, 2022

(54) X-RAY ASSISTED ELECTRON MICROSCOPY STAINING PROCEDURE

(71) Applicant: The Trustees of Princeton University, Princeton, NJ (US)

(72) Inventors: Adrian A. Wanner, Princeton, NJ (US); David Tank, Princeton, NJ (US); Sebastian Seung, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 265 days.

(21) Appl. No.: 16/681,028

(22) Filed: Nov. 12, 2019

(65) Prior Publication Data

US 2020/0150063 A1 May 14, 2020

Related U.S. Application Data

(60) Provisional application No. 62/812,041, filed on Feb. 28, 2019, provisional application No. 62/760,329, filed on Nov. 13, 2018.

(51) Int. Cl.
*G01N 23/2251* (2018.01)
*G01N 23/046* (2018.01)
(Continued)

(52) U.S. Cl.
CPC ......... *G01N 23/2251* (2013.01); *A61B 6/035* (2013.01); *G01N 1/30* (2013.01); *G01N 23/046* (2013.01); *G01N 1/31* (2013.01); *G01N 13/00* (2013.01); *G01N 23/225* (2013.01); *G01N 2013/003* (2013.01); *G01N 2223/419* (2013.01); *G01N 2223/6126* (2013.01)

(58) Field of Classification Search
CPC ...... G01N 1/31; G01N 1/30; G01N 2223/419; G01N 2223/6126; G01N 2013/003; G01N 13/00; G01N 23/225; G01N 23/2251; G01N 23/046; A61B 6/035
See application file for complete search history.

(56) References Cited

U.S. PATENT DOCUMENTS 9,958,362 B1 * 5/2018 Roper ................. G01N 1/312
11,123,732 B2 * 9/2021 Kelly ................. G01N 33/6848
(Continued)

OTHER PUBLICATIONS

Lin, Q., et al., "Optimization of image quality and acquisition time for lab-based X-ray microtomography using an iterative reconstruction algorithm," Advances in Water Resources, vol. 115 (May 2018), pp. 112-124.
(Continued)

*Primary Examiner* — Dani Fox
*Assistant Examiner* — Soorena Kefayati
(74) *Attorney, Agent, or Firm* — Meagher Emanuel Laks Goldberg & Liao, LLP

(57) ABSTRACT

Disclosed are a procedure and system for live monitoring of staining quality and heavy metal diffusion during electron microscopy preparation protocols for biological samples. The disclosed approach employs x-rays via, e.g., a commercially available micro-CT device, to observe and measure the diffusion and distribution of the heavy metals during conventional biological sample staining procedures for electron microscopy. This allows one to observe and check the quality and homogeneity of the staining without damaging or destroying the sample.

20 Claims, 8 Drawing Sheets

(51) Int. Cl.
  *A61B 6/03*     (2006.01)
  *G01N 1/30*     (2006.01)
  *G01N 1/31*     (2006.01)
  *G01N 23/225*   (2018.01)
  *G01N 13/00*    (2006.01)

(56) References Cited

U.S. PATENT DOCUMENTS

| | | | | |
|---|---|---|---|---|
| 2004/0099805 | A1* | 5/2004 | Ochiai | H01J 37/265 |
| | | | | 250/311 |
| 2005/0173632 | A1* | 8/2005 | Behar | B01L 3/508 |
| | | | | 250/311 |
| 2007/0172100 | A1* | 7/2007 | Lefebvre | G01N 15/1475 |
| | | | | 382/128 |
| 2008/0088831 | A1* | 4/2008 | Mulders | G01N 1/30 |
| | | | | 356/237.2 |
| 2009/0080600 | A1* | 3/2009 | Keller | A01K 1/031 |
| | | | | 378/18 |
| 2010/0143198 | A1* | 6/2010 | Damiano, Jr. | G01N 23/046 |
| | | | | 216/2 |
| 2011/0181701 | A1* | 7/2011 | Varslot | G01N 33/241 |
| | | | | 348/46 |
| 2012/0093286 | A1* | 4/2012 | Peterson | G01N 23/223 |
| | | | | 378/45 |
| 2012/0321037 | A1* | 12/2012 | Ogura | G01N 23/2251 |
| | | | | 378/208 |
| 2013/0221217 | A1* | 8/2013 | Shiono | H01J 37/28 |
| | | | | 250/307 |
| 2014/0301528 | A1* | 10/2014 | La Riviere | G01N 23/046 |
| | | | | 378/62 |
| 2014/0360286 | A1* | 12/2014 | Carragher | H01J 37/261 |
| | | | | 73/863.11 |
| 2015/0090899 | A1* | 4/2015 | Carragher | H01J 37/20 |
| | | | | 250/428 |
| 2015/0144490 | A1* | 5/2015 | Deisseroth | G01N 1/40 |
| | | | | 204/461 |
| 2016/0123855 | A1* | 5/2016 | Friedrich | G01N 1/36 |
| | | | | 427/58 |
| 2016/0274101 | A1* | 9/2016 | Bartko | C12M 25/00 |
| 2017/0160211 | A1* | 6/2017 | Schulte | G01N 23/046 |
| 2017/0207062 | A1* | 7/2017 | Dufresne | G01N 1/312 |
| 2017/0336706 | A1* | 11/2017 | Wang | A61B 6/547 |
| 2018/0045623 | A1* | 2/2018 | Deisseroth | G01N 1/31 |
| 2018/0045623 | A1* | 2/2018 | Ragan | G02B 21/26 |
| 2018/0218878 | A1* | 8/2018 | Xu | H01J 37/28 |
| 2018/0306688 | A1* | 10/2018 | Hwu | G01N 1/36 |
| 2018/0356321 | A1* | 12/2018 | Sase | G01N 1/30 |
| 2019/0113423 | A1* | 4/2019 | Goodman | G06V 20/698 |
| 2020/0057007 | A1* | 2/2020 | Ezure | G01N 33/4833 |
| 2021/0270705 | A1* | 9/2021 | Van Der Zaag | A61B 10/0283 |

OTHER PUBLICATIONS

Soleimani, et al., "Introduction: a brief overview of iterative algorithms in X-ray computed tomography", Philos Trans A Math Phys Eng Sci Jun. 13, 2015; 373(2043): 20140399.

Nien, et al., "Relaxed Linearized Algorithms for Faster X-Ray CT Image Reconstruction", IEEE Trans Med Imaging. Apr. 2016;35(4):1090-8.

Hua et al., "Large-volume en-bloc staining for electron microscopy-based connectomics", Nat Commun 6, 7923 (2015).

Mikula et al., "High-resolution whole-brain staining for electron microscopic circuit reconstruction", Nat Methods. Jun. 2015; 12(6):541-6).

White et al., "A chemical mechanism fortissue staining by osmium tetroxide-ferrocyanide mixtures", J Histochem Cytochem. 1979 27:1084.

Leica Mikrosysteme GmbH: Tissue Processor Leica EM TP, Leica EM TP Brochure Jul. 2016 https://www.leicamicrosystems.com/products/sample-preparation-for-electron-microscopy/tissueprocessors/details/product/leica-em-tp/.

Carl Zeiss Microscopy GmbH: Xradia Versa Family, downloaded Nov. 12, 2019 https://www.zeiss.com/microscopy/us/products/x-raymicroscopy/zeiss-xradia-520-versa.html.

* cited by examiner

X-RAY ASSISTED ELECTRON MICROSCOPY STAINING PROCEDURE

CROSS-REFERENCE TO RELATED APPLICATIONS

This application claims priority to U.S. Provisional App. No. 62/760,329 filed Nov. 13, 2018, and U.S. Provisional App. No. 62/812,041 filed Feb. 28, 2019, both of which are hereby incorporated in their entirety by reference.

STATEMENT REGARDING FEDERALLY SPONSORED RESEARCH OR DEVELOPMENT

This invention was made with government support under Grant No. NS104648 awarded by the National Institutes of Health. The government has certain rights in the invention.

BACKGROUND

Typical electron microscopy staining protocols for biological samples consist of several steps in which a sample (e.g., a piece of brain tissue) is immersed in various heavy metal solutions. These heavy metals react with and bind to lipids, proteins or DNA and thereby stain these macromolecules and cellular structures. In thick samples, however, it is difficult to establish homogeneous staining throughout the sample, mainly because of different diffusion kinetics in different regions of the sample. So far, the quality and homogeneity of the staining could only be assessed after the whole staining protocol has been conducted, including a final embedding step in an Epoxy resin. A typical staining protocol takes several days until the usual assessment by electron microscopy is possible. That assessment involves cutting the sample into ultrathin sections that can be viewed in an electron microscope, which is a destructive and very time-consuming process.

BRIEF SUMMARY

A first aspect of the present disclosure is a method for measuring diffusion and distribution of heavy metals during biological sample staining procedures for electron microscopy. The method generally includes providing an x-ray source and x-ray detector, as well as a sealable container, such as a glass vial, that is at least partially transparent to x-rays. Then, at each staining step, immersing a sample in a heavy metal staining solution in the sealable container, irradiating the sample, and measuring differential transmission of x-rays from the x-ray source through the sample with the x-ray detector, wherein intensity of the transmitted x-rays varies depending on local particle density and heavy metal content of the sample.

Optionally, the method may include placing the sealable containers in a sample cassette inside a miniature fume hood that has been configured to be used with a device comprising the x-ray source and the x-ray detector, such as a micro computed tomography (micro-CT) device. Optionally, the x-ray detector is a two-dimensional x-ray detector.

Optionally, the sample can be rotated, e.g., by rotating the sample container or rotating a sample cassette containing the sample container. The method may optionally involve reconstructing a three-dimensional distribution of the heavy metals in the sample by rotating the sample in some fashion and acquiring at least two different images, projections, or a combination thereof.

Optionally, the method may include extracting any airborne chemicals that evaporate from the heavy metal staining solution, which may be accomplished through the use of a fume hood, such as a miniature fume hood. Optionally, a sample cassette containing the sample container is configured for fully automated tissue processing.

Optionally, the method may include comparing the differential transmission of x-rays through the sample with a second differential transmission of x-rays through the sample detected at a later point in time, and/or comparing a three-dimensional distribution of heavy metals within the sample at a first point in time with a three-dimensional distribution of heavy metals within the sample at a later point in time.

A second aspect of the present disclosure is a system for measuring diffusion and distribution of heavy metals during biological sample staining procedures for electron microscopy. The system includes a sealable container that is at least partially transparent to x-rays, a fume hood configured to hold a sample cassette having a sample in a heavy metal staining solution within the sealable container, and an x-ray detector configured to detect differential transmission of x-rays from an x-ray source through the sample, wherein intensity of the transmitted x-rays varies depending on local particle density and heavy metal content of the sample.

Optionally, the sealable containers or sample cassette can be rotated. Optionally, the x-ray detector is a two-dimensional x-ray detector. Optionally, the x-ray source and x-ray detector are components within a micro computed tomography (micro-CT) device. Optionally, the system includes at least one processor configured to control the system, including, e.g., reconstructing a three-dimensional distribution of the heavy metals in the sample by rotating the sample and acquiring at least two different images, projections, or a combination thereof, compare the differential transmission of x-rays through the sample with a second differential transmission of x-rays through the sample detected at a later point in time, and/or compare a three-dimensional distribution of heavy metals within the sample at a first point in time with a three-dimensional distribution of heavy metals within the sample at a later point in time.

Optionally, the fume hood is configured to extract any airborne chemicals that evaporate from the staining solution. Optionally, the sample cassette is configured to enable a fully automated tissue processing. Optionally, the resolution of the system is between 100 nm and 5 μm. Optionally, the system may provide an indication of tissue expansion or shrinkage.

DETAILED DESCRIPTION

A first aspect of the present disclosure is drawn to a method for measuring diffusion and distribution of heavy metals during biological sample staining procedures for electron microscopy.

Figure 1:
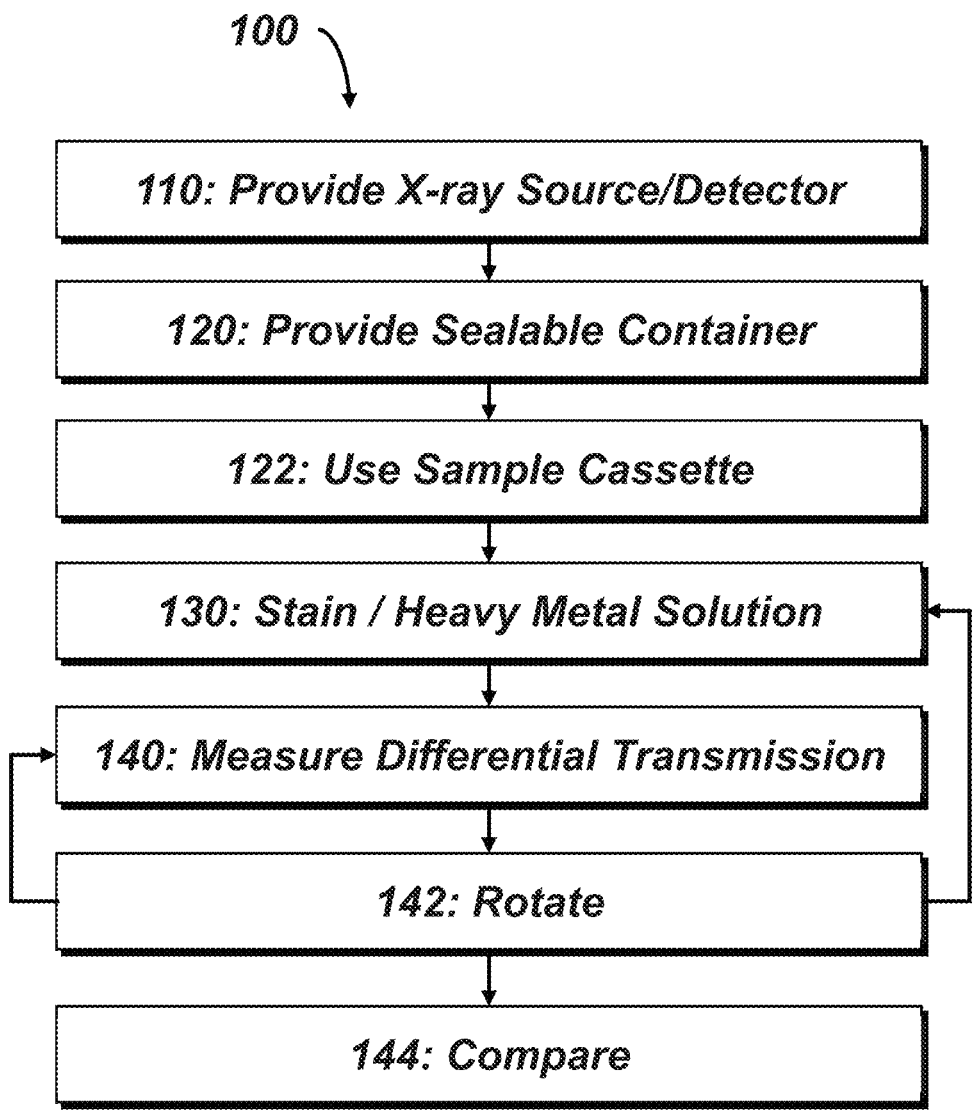
FIG. 1 is a flowchart of an embodiment of the disclosed method.

The method can be understood in reference to FIG. 1. In FIG. 1, the method (100) begins by an x-ray source and x-ray detector (110). The x-ray source and detector may be separate components or may be provided all as part of a single device. For example, the source and detector may be a part of a micro computed tomography (micro-CT) devices (which as used herein includes nano computed tomography (nano-CT) devices as well).

The x-ray source may be any appropriate source as understood by those of skill in the art. The x-ray source usually comprises an x-ray tube within a protective housing. For example, in some approaches, x-rays are generated in a vacuum tube by directing electrons produced in a cathode at a target (e.g., tungsten, copper, etc.), which emits x-rays in response. The x-rays are then transmitted in the shape of a cone through ports, slits, and/or diaphragms, etc., towards a sample.

The x-ray detector may be any appropriate detector as understood by those of skill in the art. For example, the detector may be a silicon drift detector, a pixel detector, or a flat panel detector.

The x-ray detector may be a two-dimensional x-ray detector.

The method also requires providing a sealable container (120) that is at least partially transparent to x-rays. In some embodiments, the sealable container has a transmission of at least 80%, at least 85%, at least 90%, or at least 95% of x-rays within a desired wavelength range. Non-limiting examples of potential materials for the sealable container include glass, quartz, or a polymer such as Kapton® polyimides.

Non-limiting form factors for the container include vials, pouches, and capillaries.

The containers may be sealed in any appropriate manner. For example, parafilm may be used to cover an opening in the container or closing the ends of an open cylinder with thin (typically less than 25.4 μm (1 mil), e.g., ~6 μm thick) Mylar® polyester films or Kapton® polyimide films.

Optionally, a sample cassette may be used (122). The sample cassette may be any shape, including relatively thin, disc-like shapes or square shapes. The sample cassette will also generally be comprised of materials that are at least partially transparent to x-rays. In some embodiments, the sample cassette has a transmission of at least 80%, at least 85%, at least 90%, or at least 95% of x-rays within a desired wavelength range.

When a sample cassette is used, typically this will involve placing the sealable containers within certain fixed positions in a sample cassette. The sample cassette may be placed inside a miniature fume hood, such as one that has been configured to work with a micro-CT device.

In some embodiments, the sample cassette containing the sample container may be configured for fully automated tissue processing. Specifically, in some embodiments, the cassette is configured to also allow the operator tight control over the temperature of the individual vials/solutions (e.g., +/-1° C.) as some staining steps have to be performed at low temperatures (e.g., at 4° C.) or at higher temperatures (e.g., at 50° C. or 60° C.) and allows a system using the cassette to exchange staining solutions automatically.

The method continues by immersing the sample, at each staining step, in a heavy metal staining solution in the sealable container (130).

The staining steps are related to those used for staining in electron microscopy. The staining solutions contain heavy metals, such as osmium, uranium, or lead. While the use of one of these stains alone could be quite practical for routine purposes, the highest contrast is typically obtained when both of these stains are used in sequence, "multi contrasting", with, e.g., osmium, reduced osmium, uranyl acetate, and lead aspartate or lead citrate.

One double contrast method utilizes en bloc staining in which thick blocks of tissue (i.e., the samples) are stained with osmium, uranyl acetate and lead aspartate The staining process can be done manually or can be automated. In one embodiment, the samples may, for example, be stained a first time by being placed into osmium or reduced osmium with potassium ferrocyanide solution. Next, the sample is placed in thiocarbohydrazide solution, followed by an additional osmium incubation step. Next, the sample gets placed in uranyl acetate (UA) solution and finally in lead aspartate solution. The different staining and incubation steps might be followed by rinsing with buffer solution or single or double distilled water. Alternatively, or in addition, the staining process may involve the sample repeatedly being placed into a staining solution for a period of time, then being removed and/or tested. Thus, preferred staining procedures will involve multiple staining steps that each involve the sample being placed into a heavy metal staining solution.

The method also includes detecting and/or measuring, at each staining step, at least one image or projection. The image or projection relates to the differential transmission of x-rays (140) from the x-ray source through the sample with the x-ray detector. The intensity of the transmitted x-rays varies depending on local particle density and heavy metal content of the sample.

The method may optionally include reconstructing a three-dimensional distribution of the heavy metals in the sample by rotating (142) the sample and acquiring at least one additional image and/or projection (for a total of at least two images and/or projections relating to differential transmission of x-rays through the sample). Numerous algorithms for reconstructing three-dimensional images based on cone-beam geometry are well known in the industry, and any known algorithm may be utilized (see, e.g., Qingyang, et al., "Optimization of image quality and acquisition time for lab-based X-ray microtomography using an iterative reconstruction algorithm," Advances in Water Resources, vol 115 (May 2018), pp. 112-24; Soleimani, et al., "Introduction: a brief overview of iterative algorithms in X-ray computed tomography", Philos Trans A Math Phys Eng Sci. 2015 Jun. 13; 373(2043): 20140399; Nien, et al., "Relaxed Linearized Algorithms for Faster X-Ray CT Image Reconstruction", IEEE Trans Med Imaging. 2016 April; 35(4):1090-8).

Various approaches may be used to capture the additional images and/or projections. In some embodiments, the source and detector are repositioned around the sample(s). In some embodiments, the samples are rotated (for example, rotating 90 degrees). In some embodiments, the sample cassette holding the samples is rotated. In some embodiments, the method uses two or more detectors, and the source moves around the sample to direct the x-rays through the sample towards each detector as needed.

Figure 2A:
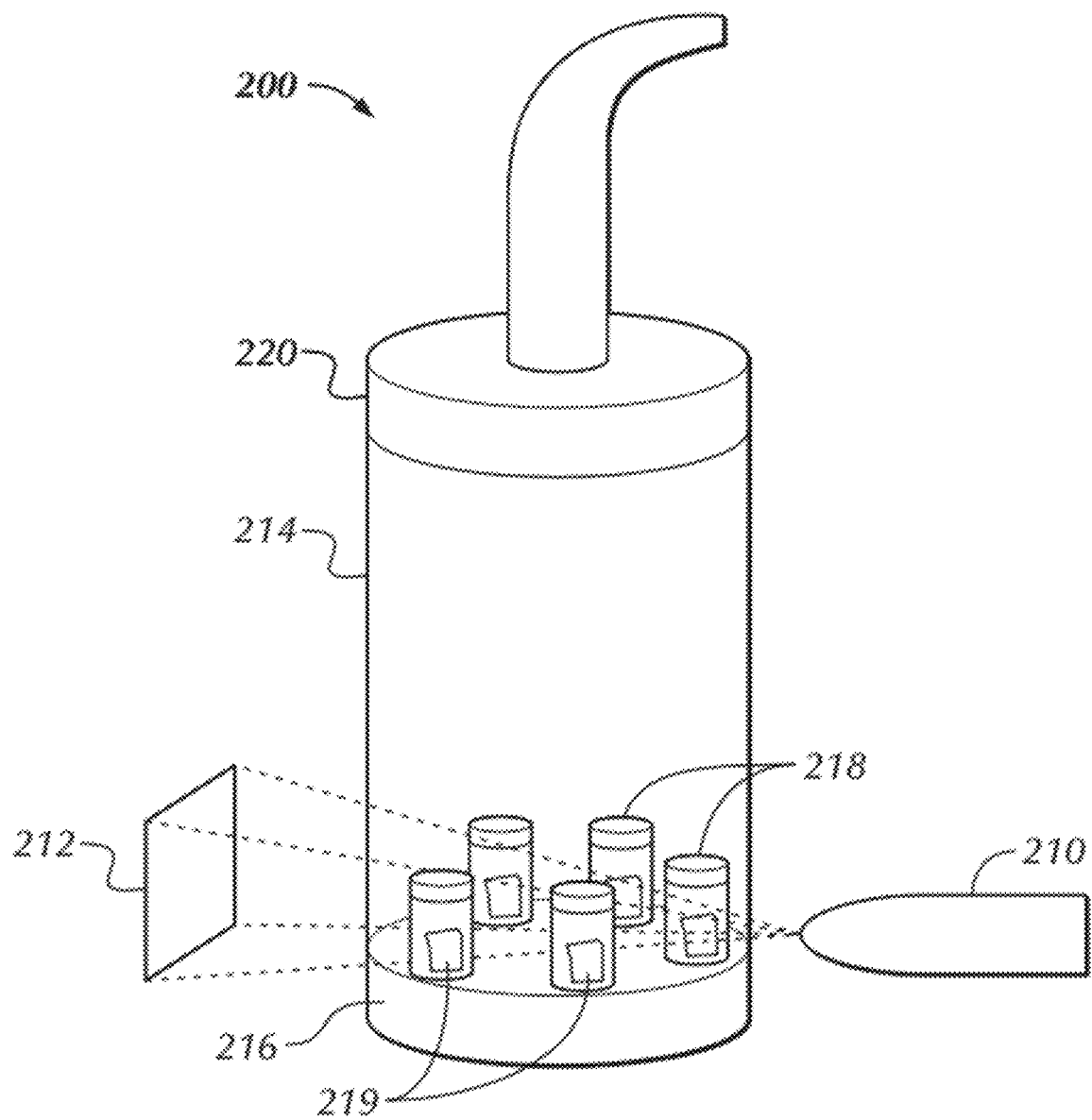
FIG. 2A is a side view of an embodiment of a disclosed system.
Figure 2B:
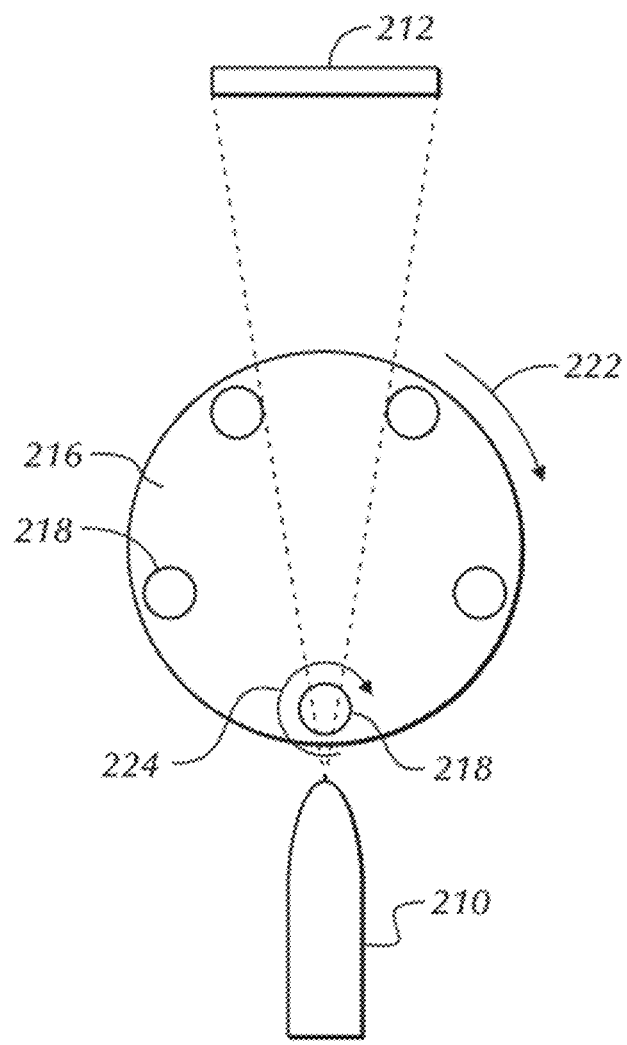
FIG. 2B is a top view of an embodiment of a disclosed system.

In some embodiments, the x-ray source only directs x-rays through a single sample at a time (see FIG. 2B). In other embodiments, the x-ray source irradiates multiple samples simultaneously, then existing image processing techniques are used to distinguish and quantify the differential transmission through each sample (for example, in one embodiment, this may be accomplished by inverting the captured image, finding the contours of each sample based on, e.g., pixel-to-pixel variation of the captured image, determining the intensities for each pixel of a given sample, and then determining differential transmission based on those intensities. In one embodiment, using inverted images, the system there is a linear correlation between pixel intensity and differential transmission at that point, with zero intensity translating to 100% transmission and a maximum intensity translating to 0% transmission through each sample at that pixel. In some embodiments, the method may involve capturing, for each sample, a set of values representing the position of the pixel (e.g., via a 2D or 3D cartesian, polar, or spherical coordinates, etc.) and a value representing an intensity and/or a differential transmission. In some embodiments, the method involves captures a date and time for each of pixel position and intensity/transmission value.

The method may include extracting any airborne chemicals that evaporate from the heavy metal staining solution by using a fume hood. This may be done at one or more discrete points in time (e.g., after staining (130) but before measuring (140) the differential transmission), or may be done continuously throughout the entire procedure(s) where the stained samples are being handled, such as throughout the staining (130), measuring (140), and rotating (142) steps.

A second aspect of the present disclosure is related to a system capable of performing the disclosed method for measuring diffusion and distribution of heavy metals during biological sample staining procedures for electron microscopy. Such a system can best be understood with reference to FIGS. 2A and 2B.

Embodiments of the system (200) will typically involve at least three components—(i) one or more sealable containers (218) for holding the sample(s) (219); (ii) an x-ray source (210); and (iii) an x-ray detector (212)—and preferably two others—(iv) a fume hood (214/220); and (v) a sample cassette (216).

As discussed above, the sealable container (218) should be at least partially transparent to x-rays. The sample cassette (216) is preferably configured to contain a plurality of sealable containers (218), where a sample (219) in a heavy metal staining solution is contained within the sealable container (218).

The fume hood (214/220) is preferably configured to hold the sample cassette (216). Note that in some embodiments, the fume hood (214/220) includes a portion of the fume hood (214) (e.g., a fixed opaque or transparent shield, a moveable sash, etc.) that the sample cassette will fit into or within, or connect with in order to improve the ability of the fume hood (214/220) to capture any/all volatile chemicals, etc., that may escape from the sealable containers. In other embodiments, the sample cassette (216) is simply under a fume hood (220), without a portion (214) that the sample cassette (216) could fit into, within, or connect with. For example, in a high-throughput arrangement, a robot arm could pick-and-place samples under a large fume hood.

Further, the fume hood as shown appears to have only a single vent, but the fume hood may have any appropriate arrangement of inlet and suction vents as understood by one of skill in the art. For example, the fume hood (214/220) could have an air inlet at the top, and a series of suction vents (not shown) around the edge of the sample cassette (216). An air inlet or suction vent could also be incorporated into or around the sample cassette (216). For example, the sample cassette could provide air to the fume hood through, e.g., a hole in an axial direction through the center of the sample cassette.

The x-ray detector (212) is configured to detect differential transmission of x-rays from an x-ray source (221) through the sample, where intensity of the transmitted x-rays varies depending on local particle density and heavy metal content of the sample. The sealable container (218) may then be rotated (224) or moved and/or the sample cassette (216) may be rotated (222) or moved as necessary to ensure the system captures sufficient x-ray images and/or projections For example, the sealable container (218) may rotate to allow the x-ray source and detector to capture images from different angles of the sample, and the sample cassette (216) may rotate to allow different sealable containers (218) to be moved into place between the x-ray source (210) and the x-ray detector (212).

Typically, the system will also include one or more processors (not shown) for controlling some or all of the other components in the system and/or processing data from the system. The processor(s) may also send information to a display via a graphical user interface, for example to show a user x-ray images, projections, and/or reconstructions. The processor(s) may also send information to a wired or wireless communications interface.

In some embodiments, at least one processor is configured to reconstruct a three-dimensional distribution of the heavy metals in the sample by causing the sample to rotate, and causing the acquisition of at least two different images, projections, or combination thereof.

In some embodiments, at least one processor is configured to compare the differential transmission of x-rays through the sample with a second differential transmission of x-rays through the sample detected at a later point in time and/or compare a three-dimensional distribution of heavy metals within the sample at a first point in time with a three-dimensional distribution of heavy metals within the sample at a later point in time.

In some embodiments, the fume hood is further configured to extract airborne chemicals that evaporate from the staining solution. This is generally understood to mean more than 99%, preferably more than 99.5%, and more preferably more than 99.9%, of the airborne chemicals that evaporate from the staining solution are not allowed to remain in the volume of space where the chemicals are being processed.

In some embodiments, the sample cassette is configured to enable a fully automated tissue processing.

In some embodiments, the resolution of the system is between 100 nm and 5 µm.

In various embodiments of the method, at a point in time after at least two differential transmissions are detected/measured, the method may also include comparing two or more differential transmission of x-rays through the sample, each taken at a different point in time. In some embodiments, this comparison occurs after at least three differential transmissions are detected/measured through the same sample, each at a different point in time. In some embodiments, the comparison occurs based on an image taken before the staining process or in the first 5 minutes after the staining process has begun, an image taken at some intermediate time during the staining process, and an image taken at the end of the staining process.

An example of this can be seen in reference to FIGS. 3A-3F, which shows time-lapse x-ray imaging of the diffusion of $OsO_4$ into a block of mouse brain tissue after being in a staining solution for 20 minutes (FIG. 3A), 1 hour (FIG. 3B), 5 hours (FIG. 3C), 9 hours (FIG. 3D), 13 hours (FIG. 3E) and 17 hours. Note that the same sample was placed into solution for a period of time, taken out and x-rayed, and then placed back into solution for another period of time, taken out and x-rayed, etc., until the full 17 hours had elapsed.

As a proof of principle for the usefulness of the X-ray assisted staining procedure, the tissue diffusion coefficient of the widely used electron microscopy staining agent $OsO_4$ was measured in two different conditions (the sample was immersed in aldehyde fixative solution for 12 hours (condition 1) and 36 hours (condition 2)). After washing, the samples were transferred to 2% $OsO_4$ solution and the diffusion of the heavy metals was observed using time-lapsed X-ray microscopy for 23 hours.

Figure 3A:
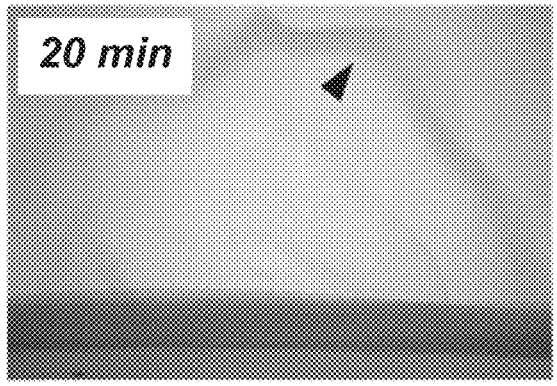
FIGS. 3A-3F are time lapse images showing the diffusion of heavy metals into brain tissue.
Figure 3B:
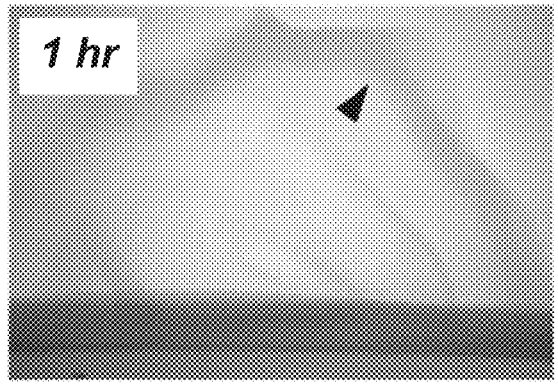
Figure 3C:
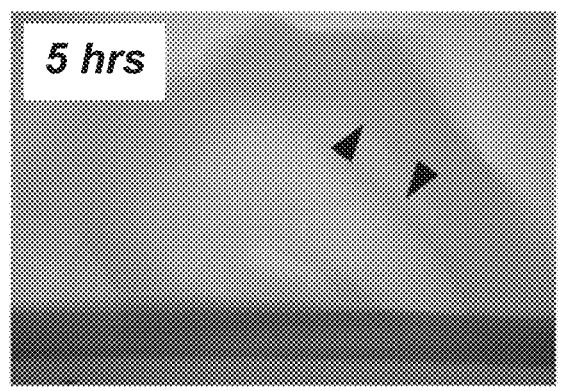
Figure 3D:
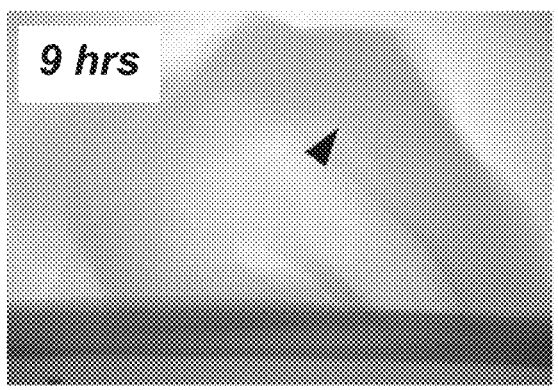
Figure 3E:
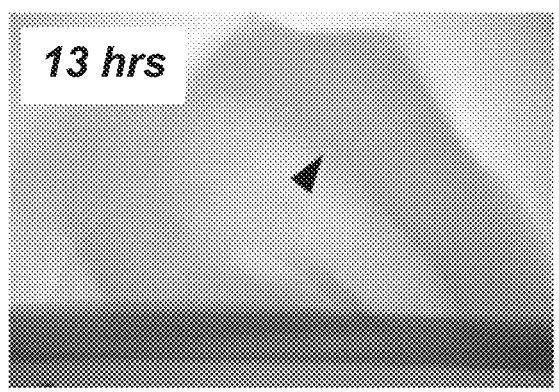
Figure 3F:
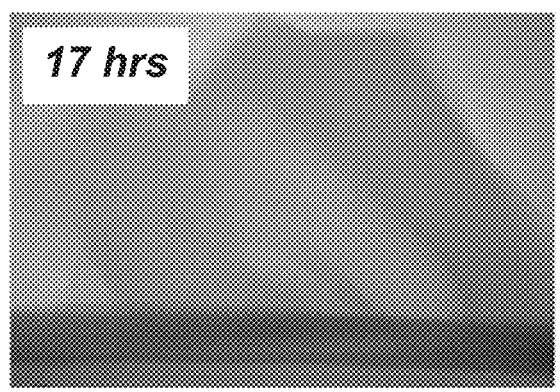
Figure 3G:
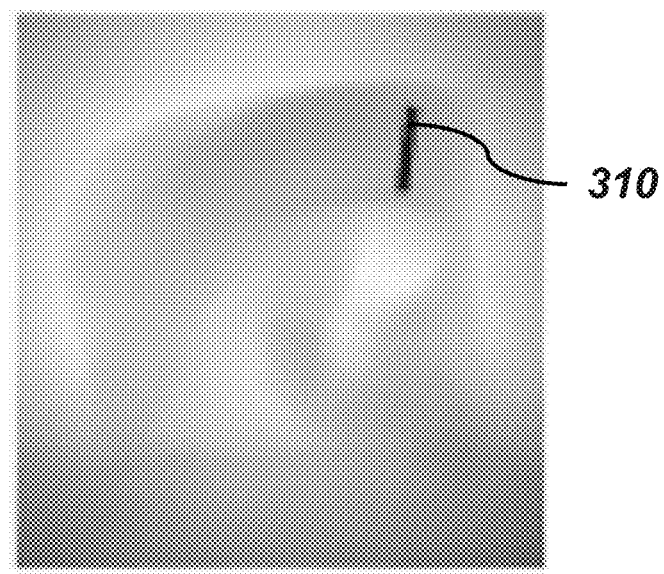
FIG. 3G is an image showing the quantification of the change in heavy metal content in different sample locations for different fixation conditions as a function of time and distance along the radial axis from the cortical surface.
Figure 3H:
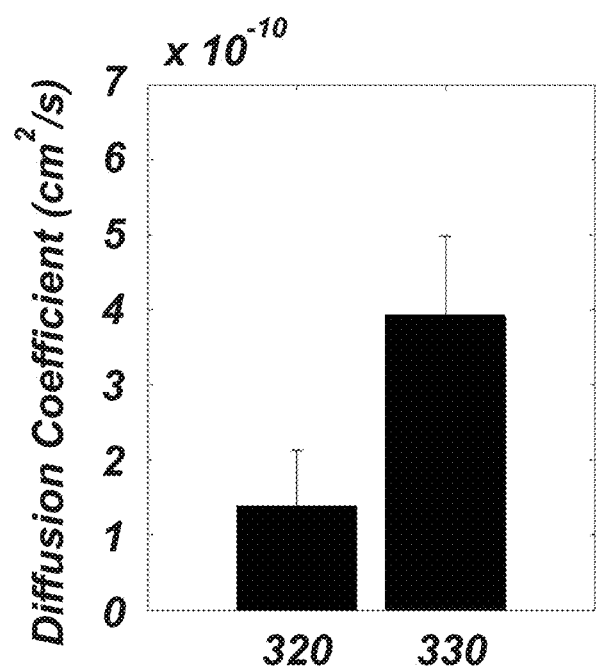
FIG. 3H is a graph showing the tissue diffusion coefficients for samples fixed for 12 hours (330) or 36 hours (320) before staining, pooled across 20 coefficient fitting repetitions for 12 ROIs out of 2 samples for each condition.

Referring to FIG. 3G, the heavy metal diffusion (310) was evaluated in radial direction towards the sample center at various starting points on the outer cortical surface. The intensity of the X-ray transmission and absorption can be used as a proxy for the amount accumulated heavy metals in the tissue. By fitting a simple diffusion model to the measured time-lapse of the heavy metal concentration into the tissue block, diffusion coefficients for the different conditions can be extracted. Referring to FIG. 3H, it was found that the diffusion coefficients in condition 1 (12 Hours of fixation, ref. 330) were on average more than 2.8 times larger than in condition 2 (36 Hours of fixation, ref. 320). Consequently, the heavy metals seem to diffuse faster and more easily in tissue with shorter fixation time resulting in more homogeneous, saturated tissue staining.

Sample Preparation

Animal use procedures were approved by the Princeton University Institutional Animal Care and Use Committee and carried out in accordance with National Institutes of Health (NIH) standards. Prior to tissue sample extraction, the mice were anesthetized by isoflurane inhalation (4%) and euthanized with an intraperitoneal injection of a ketamine (100 mg/kg) and xylazine (10 mg/kg) overdose. Next, the animal was perfused transcardially with about 250 ml fixative solution (1.31% GA and 2.5% PFA in 0.15M cacodylate buffer with 2 mM $CaCl_2$ at pH 7.4). After perfusion, the animal was left for 30 minutes on ice and the brain was removed in order to extract tissue samples using biopsy punches of 4 mm diameter. The biopsy samples were kept in fixative solution for 12 hours at 4° C. in experimental condition 1, and for 36 hours at 4° C. in experimental condition 2, respectively. Next, the samples were washed 7× for 30 minutes with 0.15M cacodylate buffer and placed in 2% $OsO_4$ in 0.15M cacodylate with 2 mM $CaCl_2$ at room temperature for 23 hours.

X-ray Microscopy

The above-described x-ray microscopy experiments were performed on a Zeiss Xradias Versa 520 3D X-ray microscope. The samples were immersed in heavy metal solution in glass containers tightly sealed with Parafilm (Bemis Company, Inc) and placed in the recording chamber of the Xradias. In the first hour, a projection image of the sample was manually acquired about every 2 minutes, followed by 22 hours of continuous acquisition of projections every 22 seconds. Acquisition parameters: voltage=100 kV, power=7 W, pixel size=2 μm,, exposure time=20 sec, filter=air Modeling The change in X-ray absorption and the corresponding accumulation of heavy metals u(x,t) along the radial direction x can be described by the diffusion coefficient K and the following diffusion/heat equation:

$$\frac{\partial u(x,t)}{\partial t} = K \cdot \frac{\partial^2 u(x,t)}{\partial x^2},$$

with the following initial conditions: u(x, t=0)=0 for $-\infty < x < \infty$, and boundary conditions:

$$u(x=0, t) = C_0 \text{ for } t > 0, \lim_{t \to \infty} u(x,t) = 0, \lim_{t \to \infty} \frac{\partial}{\partial t} u(x,t) = 0.$$

Under the given boundary and initial conditions, the above partial differential equation can be turned into a set of ordinary differential equations via the Fourier transform, which leads to the following analytical solution:

$$u(x,t) = C_0 \cdot \text{erfc}\left(\frac{x}{\sqrt{2Kt}}\right),$$

with the so called complementary Gauss error function:

$$\text{erfc}(y) = \sqrt{\frac{2}{\pi}} \int_y^\infty \exp(-\tau^2) d\tau.$$

The pixel intensities of the detected transmitted X-rays were used as a proxy for the density of heavy metal accumulation u(x,t) in the tissue, where u(x,t) was measured at various starting points on the cortical surface of the time-lapsed X-ray projections and the default trust-region-reflective algorithm of the nonlinear least-squares solver lsqnonlin in MATLAB was used to fit the model parameters $C_o$ and K.

Similarly, after reconstructing at least two three-dimensional distributions of heavy metals within the sample at different points in time, two or more of the three-dimensional distributions can be compared.

Figure 4A:
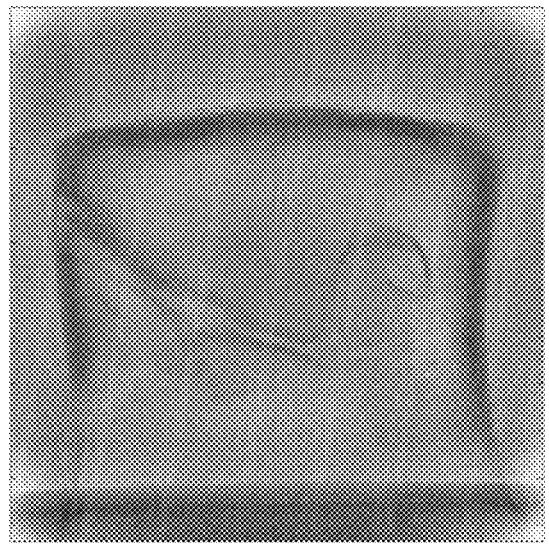
FIGS. 4A and 4B are initial (4A) and final (4B) images illustrating tissue expansion in OsO$_4$ solution.
Figure 4B:
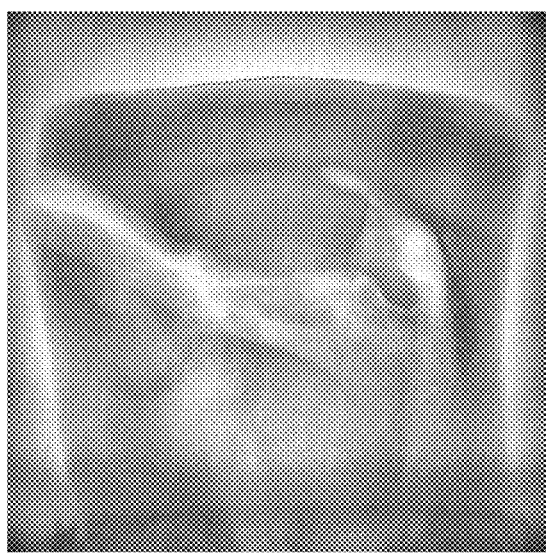
Figure 4C:
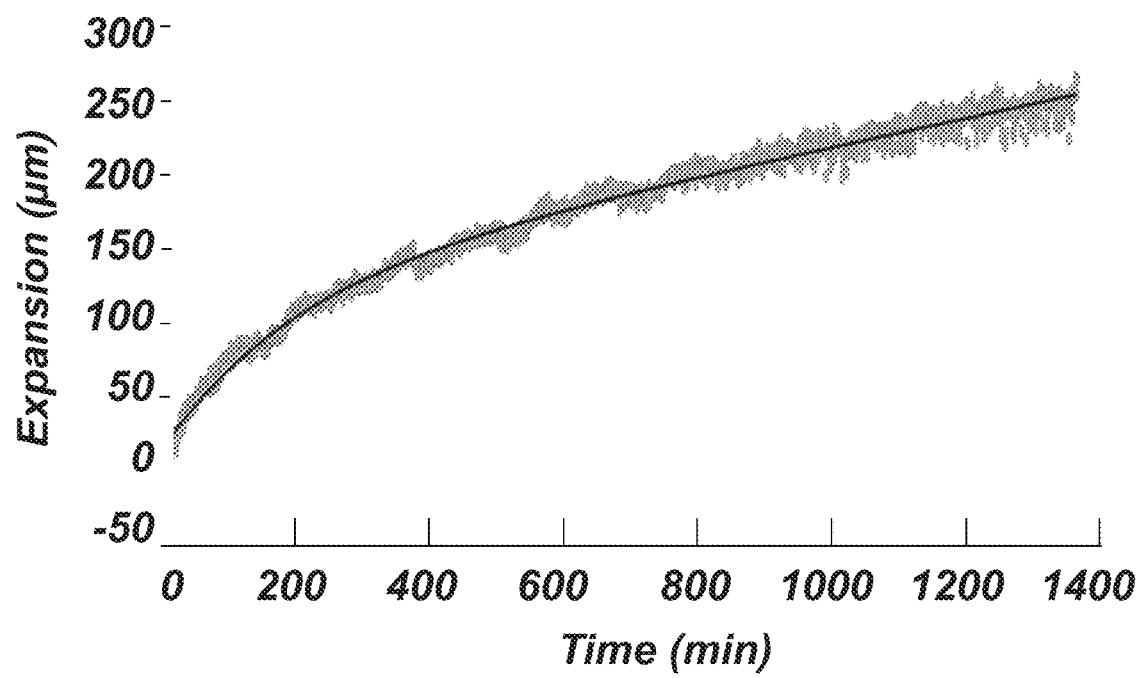
FIGS. 4C and 4D are graphs of data gathered from images of tissues in different solutions, showing tissue expansion (4C) and shrinkage (4D).
Figure 4D:
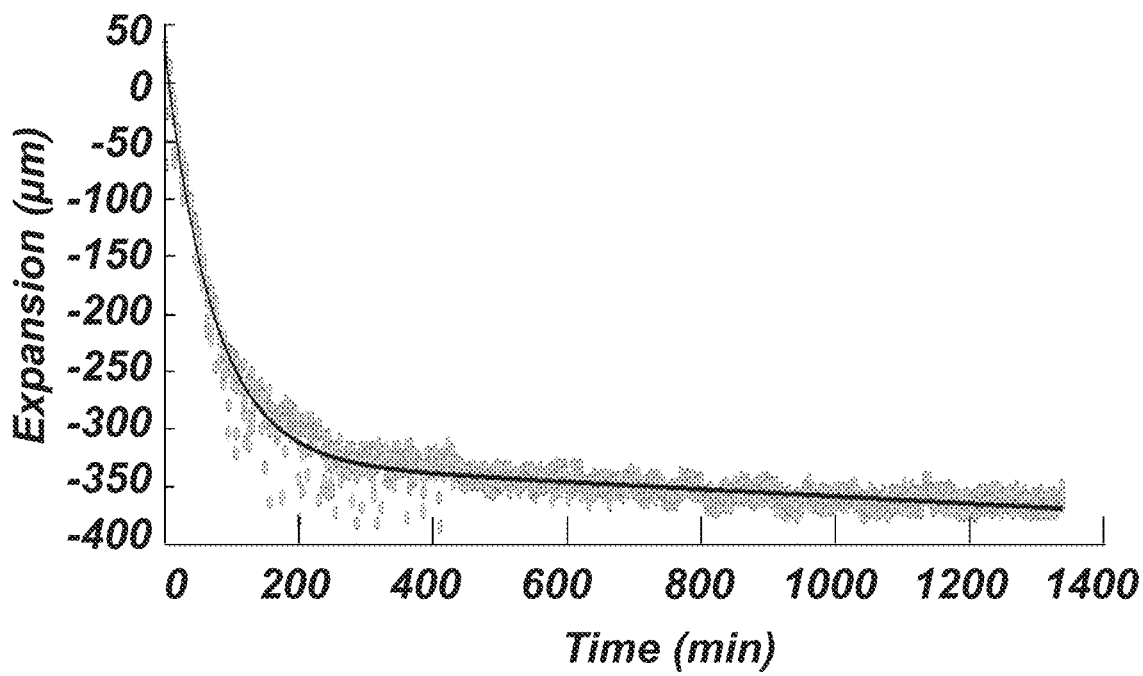
Figure 4E:
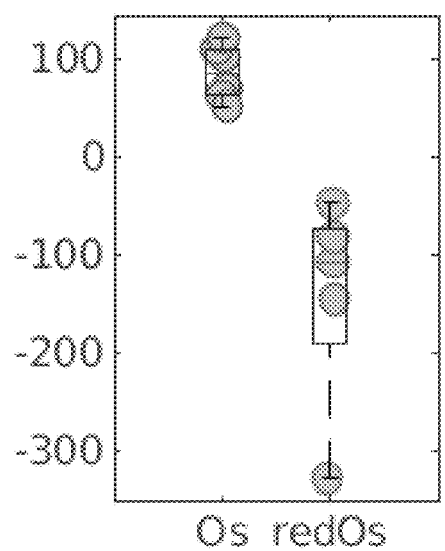
FIGS. 4E-4H are graphs for estimating the components of the model y(t)=A$_1$-A$_2$ exp(-A$_3$t)+A$_4$t for tissue expansion and/or shrinkage, for A$_1$ (4E), A$_2$ (4F), A$_3$ (4G), and A$_4$ (4H).
Figure 4F:
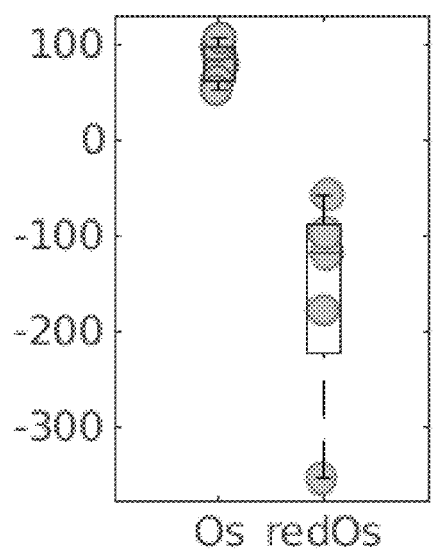
Figure 4G:
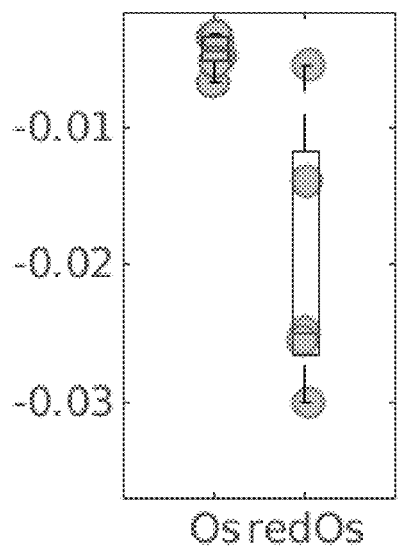
Figure 4H:
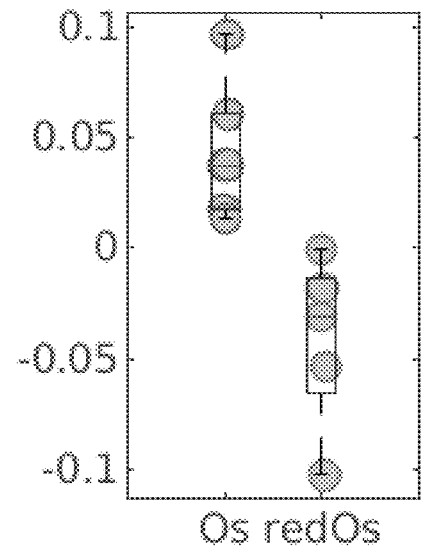

In addition to measuring diffusion constants, the disclosed method can also be used to monitor and measure other types of tissue alterations such as tissue expansion and contraction. As known by those of skill in the art, such changes in tissue conformation can result in staining artifacts and mechanical damage (see Hua et al., "Large-volume en-bloc staining for electron microscopy-based connectomics", Nat Commun 6, 7923 (2015) and Mikula et al., "High-resolution whole-brain staining for electron microscopic circuit reconstruction", Nat Methods. 2015 June; 12(6):541-6), which can be critical to detect and avoid for good ultrastructural preservation. As a proof of principle, the conformational changes of aldehyde-fixed tissue were measured during immersion in two common electron microscopy staining solutions. Solution 1 ("OS" Solution) contained 2% $OsO_4$ in 0.15M cacodylate buffer. In solution 2 ("Reduced OS" or "redOS" Solution), 2.5% potassium ferrocyanide $K_4[Fe(CN)_6]$ was added to the 2% $OsO_4$ in 0.15M cacodylate buffer, with the expectation it would form reduced osmium complexes (see White et al., "A chemical mechanism for tissue staining by osmium tetroxide-ferrocyanide mixtures", J Histochem Cytochem. 1979 27: 1084 for details). Images were captured at, e.g., multiple times during each process, including at the beginning (see, e.g., FIG. 4A for starting image for solution 1) and the end (see, e.g., FIG. 4B for final image for solution 1), which were quantified. Remarkably, the tissue expanded by several hundreds of microns in the case of solution 1 (see FIG. 4C), whereas in solution 2, the tissue shrank by several hundreds of microns (FIG. 4D). This was confirmed in multiple independent experiments. The dynamics can be well described by a simple linear expansion/shrinkage model: $y(t)=A_1-A_2 \exp(-A_3 t)+A_4 t$, where the components $A_1$, $A_2$, $A_3$, and $A_4$ can be fit to the data for different conditions. As seen in FIGS. 4E-4H, Components $A_1$ (FIG. 4E, p=0.004329), $A_2$ (FIG. 4F, p=0.004329), $A_3$ (FIG. 4G, p=0.008658), and $A_4$ (FIG. 4H, p=0.004329), were fit for Solution 1 ("OS") and Solution 2 ("redOS") data.

An embodiment of the method or system may provide an indication of tissue expansion or shrinkage. This may involve showing a graph to a user of the tissue expansion or shrinkage. This may involve detecting tissue expansion or shrinkage, determining severity of the tissue expansion or shrinkage, and/or reporting the tissue expansion or shrinkage. This may involve the use of signals for a user—for example, when displaying a number, graph, or image, the system may display one color to indicate no or minimal expansion/shrinkage, a second color to indicate significant expansion, and a third color to indicate significant shrinkage.

Embodiments of the system may store the data relating to tissue expansion or shrinkage, and/or may store representations of the data. For example, embodiments, of the system may measure tissue expansion, fit it to a model, and may store just the components of the model, rather than all of the measurements.

All patent applications, patents, and printed publications are incorporated herein by reference in the entireties, except to the extent that the incorporated material is inconsistent with the express disclosure herein, in which case the language in this disclosure controls.

Those skilled in the art will recognize or be able to ascertain using no more than routine experimentation, many equivalents to the specific embodiments of the invention described herein. Such equivalents are intended to be encompassed by the following claims.

What is claimed:

1. A method for non-destructively measuring diffusion and distribution of heavy metals during biological sample staining procedures for electron microscopy, comprising:
   providing an x-ray source and an x-ray detector;
   providing a sealable container that is at least partially transparent to x-rays;
   immersing, at each staining step in a plurality of staining steps, a sample in a heavy metal staining solution in the sealable container;
   measuring, at each staining step, differential transmission of x-rays from the x-ray source through the sample with the x-ray detector, wherein an intensity of the transmitted x-rays varies depending on local particle density and heavy metal content of the sample.

2. The method according to claim 1, further comprising placing the sealable container in a sample cassette inside a miniature fume hood configured to be used with a device comprising the x-ray source and the x-ray detector.

3. The method according to claim 1, wherein the sealable container is a glass vial.

4. The method according to claim 1, wherein the x-ray detector is a two-dimensional x-ray detector.

5. The method according to claim 1, wherein the sealable container or a sample cassette containing the sealable container can be rotated.

6. The method according to claim 1, further comprising reconstructing a three-dimensional distribution of the heavy metals in the sample by rotating the sample and acquiring at least two different images, projections, or a combination thereof.

7. The method according to claim 1, further comprising extracting any airborne chemicals that evaporate from the heavy metal staining solution by using a fume hood.

8. The method according to claim 1, wherein a sample cassette containing the sealable container is configured for fully automated tissue processing.

9. The method according to claim 2, wherein the device is a micro computed tomography (micro-CT) device.

10. The method according to claim 6, wherein the reconstructing the three-dimensional distribution occurs a first point in time and at a later point in time, and further comprising:
    detecting a second differential transmission of x-rays through the sample at a later point of time; and
    at least one of:
       comparing the differential transmission of x-rays through the sample with the second differential transmission of x-rays through the sample detected at the later point in time, or
       comparing a three-dimensional distribution of heavy metals within the sample at the first point in time with a three-dimensional distribution of heavy metals within the sample at the later point in time.

11. A system for non-destructively measuring diffusion and distribution of heavy metals during biological sample staining procedures for electron microscopy, comprising:
    a sealable container that is at least partially transparent to x-rays;
    a fume hood configured to hold a sample cassette having a sample in a heavy metal staining solution within the sealable container, wherein the sample is stained during a plurality of staining steps;
    an x-ray detector configured to detect differential transmission of x-rays from an x-ray source through the sample at each staining step of the plurality of staining steps, wherein an intensity of the transmitted x-rays varies depending on local particle density and heavy metal content of the sample; and
    at least one processor configured to:
       receive a detected differential transmission of x-rays through the sample after each staining step of the plurality of staining steps, including a first differential transmission of x-rays detected at a first point in time and a second differential transmission of x-rays detected at a second point in time; and
       compare the first differential transmission with the second differential transmission.

12. The system according to claim 11, wherein the sealable containers or sample cassette can be rotated.

13. The system according to claim 11, wherein the x-ray detector is a two-dimensional x-ray detector.

14. The system according to claim 11, wherein the x-ray source and x-ray detector are components within a micro computed tomography (micro-CT) device.

15. The system according to claim 11, wherein the at least one processor is configured to reconstruct a three-dimensional distribution of the heavy metals in the sample by rotating the sample and acquiring at least two different images, projections, or a combination thereof.

16. The system according to claim 11, wherein the fume hood is further configured to extract any airborne chemicals that evaporate from the staining solution.

17. The system according to claim 11, wherein the sample cassette is configured to enable a fully automated tissue processing.

18. The system according to claim 11, wherein a resolution of the system is between 100 nm and 5 μm.

19. The system according to claim 11, wherein the system is configured to display a graph, number, or image to provide an indication of tissue expansion or shrinkage.

20. The system according to claim 15, wherein the at least one processor is configured to reconstruct the three-dimensional distribution of heavy metals within the sample at the first point in time and reconstruct a three-dimensional distribution of heavy metals within the sample at the second; and compare the three-dimensional distribution of heavy metals within the sample at the first point in time with the three-dimensional distribution of heavy metals within the sample at the second point in time.

* * * * *